United States Patent [19]

Kameda et al.

[11] 4,123,549

[45] Oct. 31, 1978

[54] N-(3,5-DIHALOPHENYL)-α-SPIROCYCLOALKANESUCCINIMIDES, AND THEIR PREPARATION AND USE

[75] Inventors: Nobuyuki Kameda, Takarazuka; Yoshio Hisada, Kawanishi; Chiyozo Takayama, Toyonaka; Toshiro Kato, Ibaraki; Akira Fujinami, Takarazuka, all of Japan

[73] Assignee: Sumitomo Chemical Company, Limited, Osaka, Japan

[21] Appl. No.: 859,756

[22] Filed: Dec. 12, 1977

[30] Foreign Application Priority Data

Feb. 7, 1977 [JP] Japan .................................. 52-12800

[51] Int. Cl.$^2$ ..................... A61K 31/40; C07D 207/40
[52] U.S. Cl. ........................... 424/274; 260/326.5 FM
[58] Field of Search .............. 260/326.5 FM, 326.5 C; 424/274

[56] References Cited

U.S. PATENT DOCUMENTS

| | | | |
|---|---|---|---|
| 3,432,499 | 3/1969 | Rice et al. | 260/326.5 FM |
| 3,507,881 | 4/1970 | Sandberg | 260/326.5 FM |
| 3,586,697 | 6/1971 | Ozaki et al. | 260/326.5 FM |
| 3,654,306 | 4/1972 | German | 260/326.5 FM |
| 3,741,981 | 6/1973 | Fujinami et al. | 260/326.5 FM |

Primary Examiner—Jose Tovar
Attorney, Agent, or Firm—Birch, Stewart, Kolasch and Birch

[57] ABSTRACT

N-(3,5-Dihalophenyl)-α-spirocycloalkanesuccinimides of the formula:

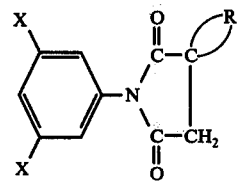

wherein X is a chlorine or bromine atom and R is a $C_3$–$C_6$ alkylene group, which show high fungicidal activities without any material toxicity to mammals and plants and which can be produced by reacting the corresponding α-spirocycloalkanesuccinic acid or its anhydride with 3,5-dichloroaniline or 3,5-dibromoaniline.

5 Claims, No Drawings

N-(3,5-DIHALOPHENYL)-α-SPIROCYCLOALKANESUCCINIMIDES, AND THEIR PREPARATION AND USE

The present invention relates to N-(3,5-dihalophenyl)-α-spirocycloalkanesuccinimides (hereinafter referred to as "N-(3,5-dihalophenyl)-succinimide(s)") of the formula:

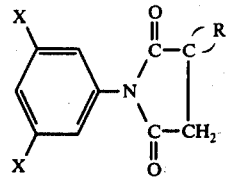

wherein X is a chlorine or bromine atom and R is a $C_3$-$C_6$ alkylene group (e.g., trimethylene, tetramethylene, pentamethylene, methylpentamethylene, hexamethylene), and their preparation and use.

It is already well known that some N-(3,5-dihalophenyl)-succinimide derivatives, of which the α- and/or β-positions are optionally substituted with various substituents, have an antimicrobial activity on certain microorganisms (e.g., U.S. Pat. Nos. 3,586,697 and 3,741,981).

As the results of an extensive study, it has now been found that the N-(3,5-dihalophenyl)-succinimides [I] having a spirocycloalkane group at the α-position exhibit an antifungal activity which is markedly superior as compared with their homologues, and in addition show no material phytotoxicity to plants (e.g., rice, kidney bean, adzuki bean, soybean, potato, tobacco, cucumber, tomato, pea, eggplant, pimento, broad bean, melon, lettuce, onion, water melon, strawberry, radish, cabbage, chinese cabbage, apple, pear, grape, peach, Japanese apricot).

The N-(3,5-dihalophenyl)-succinimides [I] have prominent effects on such a wide scope of fungi as *Cochliobolus miyabeanus, Pellicularia sasakii, Glomerella cingulata, Sclerotinia sclerotiorum, Sclerotinia cinerea, Botrytis cinerea, Alternaria mali, Sclerotinia mali, Mycosphaerella melonis, Alternaria kikuchiana, Alternaria brassicicola* and *Rhizoctonia solani*. They can control simultaneously two or more of said fungi and are quite excellent as phytopathogenic microbe-controlling agents. Also, they can effectively control *Aspergillus niger, Cladosporium herbarum* and *Chaetonium globosum* which propagate in industrial products and hence are excellent as industrial fungicides. Advantageously, they are of extremely low toxicity and have little detrimental actions on mammals and fishes.

A main object of the present invention is to provide the N-(3,5-dihalophenyl)-succinimides [I], which are useful as fungicides. Another object of this invention is to provide a process for producing the N-(3,5-dihalophenyl)-succinimides [I]. A further object of the invention is to provide fungicidal compositions containing the N-(3,5-dihalophenyl)-succinimides [I]. These and other objects and advantages of the invention will become apparent from the foregoing and subsequent descriptions.

The N-(3,5-dihalophenyl)-succinimide [I] can be prepared by reacting the corresponding spirocycloalkanesuccinic acid of the formula:

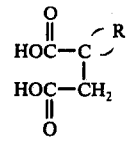

wherein R is as defined above or its anhydride, with a 3,5-dihaloaniline of the formula:

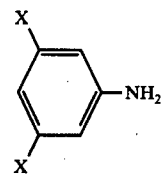

wherein X is as defined above.

Examples of typical procedures for carrying out the said preparation so as to obtain the objective N-(3,5-dihalophenyl)-succinimide [I] in good yields are as follows:

Procedure A

The starting spirocycloalkanesuccinic acid [II] or its anhydride is reacted with the 3,5-dihaloaniline [III] at a higher temperature (e.g., 170°–250° C.), or both of these compounds are heated at a lower temperature (e.g., 70°–170° C.) in the presence of an inert solvent (e.g., benzene, toluene, xylene, chlorobenzene, dichlorobenzene, methyl isobutyl ketone, cyclohexanone) and, if necessary, a catalytic amount of a base (e.g., triethylamine, tributylamine, triethanolamine, pyridine, N-methylmorpholine, potassium carbonate, sodium carbonate, sodium acetate) to give the N-(3,5-dihalophenyl)-succinimides [I].

Procedure B

The anhydride of the spirocycloalkanesuccinic acid [II] is reacted with the 3,5-dihaloaniline [III] in the presence of an inert solvent (e.g., benzene, toluene, xylene, tetrahydrofuran, dioxane, isopropyl ether, chlorobenzene), and the resulting spirocycloalkanesuccinic acid monoanilide is dehydrated in the presence of a suitable dehydrating agent (e.g., acetic anhydride, phosphorous pentoxide, phosphorus oxychloride, acetyl chloride, thionyl chloride) to give the N-(3,5-dihalophenyl)-succinimide [I].

The N-(3,5-dihalophenyl)-succinimide [I] thus produced may be purified, if necessary, by a per se conventional procedure such as recrystallization from a proper solvent.

The starting spirocycloalkanesuccinic acid [II] or its anhydride can be produced, for instance, by the process as described in M. Jackman, A. J. Bergman and S. Archer, J.Am.Chem.Soc., 70, 497 (1948) and A. Lapworth and W. Baker, Org.Syntheses, Coll. Vol. 1, 451 (1941).

In actual application as fungicides, the N-(3,5-dihalophenyl)-succinimide [I] can be used alone, but usually it is used in the form of an appropriate agricultural preparation such as dusts, wettable powders, oil sprays, tablets, emulsifiable concentrates, granules, fine granules, aerosols and the like.

These agricultural preparations can be prepared in a conventional manner by mixing the N-(3,5-dihalophenyl)-succinimide [I] with an appropriate solid or liquid carrier and appropriate adjuvants (e.g., surfactants, adherents, dispersants, stabilizers) for improving the dispersibility and other properties of the active ingredient upon use.

Examples of the solid carriers are fine powders or granules of botanical carriers (e.g., flour, tobacco stalk powder, soybean powder, walnut shell powder, wood powder, saw dust, bran, bark powder, cellulose powder, vegetable extract residue), fibrous materials (e.g., paper, corrugated cardboard, old rags), synthesized plastic powders, clays (e.g., kaolin, bentonite, fuller's earth), talcs, other inorganic minerals (e.g., pyrophyllite, sericite, pumice, sulfur powder, active carbon) and chemical fertilizers (e.g., ammonium sulfate, ammonium phosphate, ammonium nitrate, urea, ammonium chloride).

Examples of the liquid carriers are water, alcohols (e.g., methyl alcohol, ethyl alcohol), ketones (e.g., acetone, methyl, ethyl ketone), ethers (e.g., diethyl ether, dioxane, cellosolve, tetrahydrofuran), aromatic hydrocarbons (e.g., benzene, toluene, xylene, methyl naphthalene), aliphatic hydrocarbons (e.g., gasoline, kerosene, lamp oil), esters, nitriles, acid amides (e.g., dimethylformamide, dimethylacetamide), halogenated hydrocarbons (e.g., dichloroethane, carbon tetrachloride), etc.

Examples of the surfactants are alkyl sulfuric esters, alkyl sulfonates, alkylaryl sulfonates, polyethylene glycol ethers, polyhydric alcohol esters, etc. Examples of adherents and dispersants may include casein, gelatin, starch powder, carboxymethyl cellulose, gum arabic, alginic acid, lignin, bentonite, molasses, polyvinyl alcohol, pine oil and agar. As the stabilizers, there may be used PAP (isopropyl acid phosphates mixture), TCP (tricresyl phosphate), tolu oil, epoxidized oil, various surfactants, and various fatty acids and esters thereof.

The foregoing preparations generally contain 0.1 to 95.0% by weight, preferably 1 to 80% by weight of the active ingredient (including other ingredients optionally mixed therewith). A suitable amount of the preparations applied is generally 10 g to 1000 g/10 are, and the concentration of the preparations applied is preferably within the range of 0.01 to 0.1% by weight. Since, however, the amount and concentration depend upon the preparation forms, application times, application methods, application sites, diseases and crops, they may be properly increased or decreased irrespective of the aforesaid ranges.

Further, the N-(3,5-dihalophenyl)-succinimide [I] may be used in admixture with other fungicides such as, for example, N-(3,5-dichlorophenyl)-1,2-dimethylcyclopropane-1,2-dicarboximide, S-n-butyl-S'-p-tert-butylbenzyl-N-3-pyridyldithiocarbonimidate, O,O-dimethyl-O-2,6-dichloro-4-methylphenylphosphorothioate, methyl N-benzimidazol-2-yl-N-(butylcarbamoyl)-carbamate, N-trichloromethylthio-4-cyclohexene-1,2-dicarboximide, cis-N-(1,1,2,2-tetrachloroethylthio)-4-cyclohexene-1,2-dicarboximide, Polyoxin, Streptomycin, zinc ethylene-bis(dithiocarbamate), zinc dimethylthiocarbamate, manganese ethylene-bis(dithiocarbamate), bis(dimethylthiocarbamoyl)disulfide, tetrachloroisophthalonitrile, 8-hydroxyquinoline, dodecylguanidine acetate, 5,6-dihydro-2-methyl-1,4-oxathiine-3-carboxanilide, N'-dichlorofluoromethylthio-N,N-dimethyl-N'-phenylsulfamide, 1-(4-chlorophenoxy)-3,3-dimethyl-1-(1,2,4-triazol-1-yl)-2-butanone, 1,2-bis(3-methoxycarbonyl-2-thioureido)benzene and the like; and the N-(3,5-dihalophenyl)-succinimide [I] may be used in admixture with insecticides such as, for example, O,O-dimethyl-O-(4-nitro-m-tolyl)phosphorothioate, O-p-cyanophenyl-O,O-dimethylphosphorothioate, O-p-cyanophenyl-O-ethylphenylphosphonothioate, O,O-dimethyl-S-(N-methylcarbamoylmethyl)phosphorodithioate, 2-methoxy-4H-1,3,2-benzodioxaphosphorine-2-sulfide, O,O-dimethyl-S'-(1-ethoxycarbonyl-1-phenylmethyl)phosphorodithioate, α-cyano-3-phenoxybenzyl-2-(4-chlorophenyl)isovalerate, 3-phenoxybenzyl-2,2-dimethyl-3-(2,2-dichlorovinyl)cyclopropanecarboxylate, 3-phenoxybenzyl chrysanthemate and the like; and, in every case, the controlling effects of the individual chemicals are not decreased. Accordingly, simultaneous control of two or more pests and injurious insects is possible. In addition thereto, they may be used in admixture with such agricultural chemicals as miticides and with fertilizers.

Practical and presently preferred embodiments of the present invention are illustratively shown in the following examples, wherein parts and % are by weight.

EXAMPLE 1

Preparation of the N-(3,5-dihalophenyl)-succinimides [I]:

Procedure A

In a 100 ml four necked flask equipped with a water separator, a mixture containing 5.2 g of α,α-tetramethylenesuccinic acid, 4.8 g of 3,5-dichloroaniline, 0.3 g of triethylamine and 50 ml of xylene was refluxed for 3 hours. After removal of the solvent, the residue was recrystallized from ethanol to give 6.9 of N-(3,5-dichlorophenyl)-α-spirocyclopentanesuccinimide. M.P. 97.5°–98.0° C.

Anal. Calcd. for $C_{14}H_{13}NCl_2O_2$: C, 56.4; H, 4.4; N, 4.7; Cl, 23.8. Found: C, 56.3; H, 4.5; N, 4.4; Cl, 23.8.

Procedure B

A mixture containing 9.6 g of α,α-pentamethylenesuccinic anhydride, 8.9 g of 3,5-dichloroaniline and 100 ml of toluene was refluxed for 1 hour. After cooling, the resulting mixture was admixed with 20 g of acetic anhydride and 0.5 g of sodium acetate and refluxed for 2 hours. The reaction mixture was poured into 100 ml of water. The precipitate was collected by filtration, washed with water and dried in vacuum to give 14.6 g of N-(3,5-dichlorophenyl)-α-spirocyclohexanesuccinimide. M.P. 132.0°–133.0° C.

Anal. Calcd. for $C_{15}H_{15}NCl_2O_2$: C, 57.7; H, 4.9; N, 4.5; Cl, 22.7. Found: C, 57.8; H, 5.2; N, 4.2; Cl, 22.3.

In the same manner as above, the N-(3,5-dihalophenyl)-succinimides [I] as shown in Table 1 were prepared:

Table 1

| Starting materials | | | Produced N-(3,5-dihalophenyl)-succinimides [I] | | | | | | | |
|---|---|---|---|---|---|---|---|---|---|---|
| Spirocycloalkane-succinic acid [II] or its anhydride | 3,5-Dihaloaniline [III] | Procedure | No. | Chemical structure | Melting point (°C) | Yield (%) | Elementary analysis (%) | | | |
| | | | | | | | C | H | N | Cl |
| (cyclobutane with two -COOH) | (3,5-dibromoaniline) | A | 1 | (N-(3,5-dibromophenyl) spirocyclobutane succinimide) | 159.5–162.5 | 87 | 41.9 (42.1) | 3.0 (2.8) | 3.8 (4.0) | (Br) 42.8 (42.6) |
| (cyclopentane with two -COOH) | (3,5-dichloroaniline) | A | 2 | (N-(3,5-dichlorophenyl) spirocyclopentane succinimide) | 97.5–98.0 | 78 | 56.4 (56.3) | 4.4 (4.5) | 4.7 (4.4) | 23.8 (23.8) |
| (cyclohexane with -CO-O-CO anhydride) | (3,5-dichloroaniline) | B | 3 | (N-(3,5-dichlorophenyl) spirocyclohexane succinimide) | 132.0–133.0 | 85 | 57.7 (57.8) | 4.9 (5.2) | 4.5 (4.2) | 22.7 (22.3) |
| (cyclohexane with CH$_3$ and two -COOH) | (3,5-dichloroaniline) | A | 4 | (N-(3,5-dichlorophenyl) methyl-spirocyclohexane succinimide) | 127.0–129.5 | 83 | 58.9 (58.8) | 5.3 (5.1) | 4.3 (4.5) | 21.7 (21.3) |
| (cycloheptane with two -COOH) | (3,5-dichloroaniline) | A | 5 | (N-(3,5-dichlorophenyl) spirocycloheptane succinimide) | 128.5–131.0 | 76 | 58.9 (59.2) | 5.3 (5.5) | 4.3 (4.3) | 22.7 (22.2) |
| (cyclohexane with two -COOH) | (3,5-dibromoaniline) | A | 6 | (N-(3,5-dibromophenyl) spirocyclohexane succinimide) | 157.0–158.0 | 85 | 44.9 (44.7) | 3.8 (3.5) | 3.5 (3.8) | (Br) 39.9 (40.2) |

Note:
In the elemental analysis, the values as calculated are unparenthesized, and the values as found are parenthesized.

Example 2

Formulation of compositions:

(a) Dust

Two parts of the compound (2) and 98 parts of clay were thoroughly pulverized and mixed together to obtain a dust containing 2% of the active ingredient. In application, the dust was dusted as such.

(b) Dust

One part of the compound (3) and 99 parts of talc were thoroughly pulverized and mixed together to obtain a dust containing 1% of the active ingredient. In application, the dust was dusted as such.

(c) Wettable powder

Fifty parts of the compound (4), 5 parts of a wetting agent of the alkylbenzenesulfonate type and 45 parts of diatomaceous earth were thoroughly pulverized and mixed together to obtain a wettable powder containing 50% of the active ingredient. In application, the wettable powder was diluted with water, and the resulting dilution was sprayed.

(d) Wettable powder

Eighty parts of the compound (1), 5 parts of a wetting agent of the alkylbenzenesulfonate type and 15 parts of white carbon were throughly pulverized and mixed together to obtain a wettable powder containing 80% of the active ingredient. In application, the wettable powder was diluted with water, and the resulting dilution was sprayed.

(e) Emulsifiable concentrate

Ten parts of the compound (1), 40 parts of dimethyl sulfoxide, 40 parts of xylene and 10 parts of an emulsifier of the polyoxyethylene dodecylphenol ether type were mixed together to obtain an emulsifiable concentrate containing 10 % of the active ingredient. In application, the emulsifiable concentrate was diluted with water, and the resulting dilution was sprayed.

(f) Granule

Five parts of the compound (6), 93.5 parts of clay and 1.5 parts of a binder of the polyvinyl alcohol type were thoroughly pulverized and mixed together, kneaded with water and then granulated and dried to obtain a granule containing 5% of the active ingredient.

The following examples show some typical test data supporting the excellent activity of the N-(3,5-dihalophenyl)-succinimides [I]. In these examples, the compound numbers corresponds to those in Table 1.

EXAMPLE 3

Protective activity test on Sclerotinia rot of kidney bean (*Sclerotinia sclerotiorum*):

When kidney bean (var.: Taishō-kintoki) were grown up to the beginning of a third true leaf stage in a flower pot of 9 cm in diameter, each of the wettable powders of the test compounds was diluted with water and sprayed on the kidney beans at a rate of 10 ml per pot. After 1 day, the leaves of the kidney beans were inoculated with the mycelial disc (5 mm in diameter) of *Sclerotinia sclerotiorum*. After 3 more days, the infectious state was observed. The degree of infection was examined by the following method: the leaves examined were measured for a percentage of infected area and classified into the corresponding disease indices, 0, 1, 2, 3, 4, 5; the leaves belonging to the same disease indices were summed up, $n_0$, $n_1$, $n_2$, $n_3$, $n_4$, $n_5$; and the disease severity was calculated according to the following equation.

| Disease index | Percentage of infected area |
|---|---|
| 0 | No infection |
| 1 | Slight infection around the inoculum |
| 2 | Infected area of about 1/5 of the inoculated leaf |
| 3 | Infected area of about 2/5 of the inoculated leaf |
| 4 | Infected area of about 3/5 of the inoculated leaf |
| 5 | Infected area of 3/5 or more of the inoculated leaf |

$$\text{Disease severity (\%)} = \frac{0 \times n_0 + 1 \times n_1 + \ldots + 5 \times n_5}{5 \times n} \times 100$$

The results of this test are shown in Table 2. As is apparent from the test results, the compounds of the present invention show a higher protective activity than the control compound.

Table 2

| Test compound | Concentration of active ingredient (ppm) | Disease severity (%) |
|---|---|---|
| 1 | 100 | 0 |
| 2 | 100 | 0 |
| 3 | 100 | 0 |
| 4 | 100 | 0 |
| 5 | 100 | 0 |
| 6 | 100 | 0 |
|  | 100 | 32.7 |
| No treatment | — | 100 |

Note:
*)Commercially available fungicide, generic name "Benomyl".

EXAMPLE 4

Protective activity test on gray mold of cucumber (*Botrytis cinerea*):

When cucumber (var.: Sagami-hanjiro) was grown up to the full extent of a first true leaf stage in a flower pot of 9 cm in diameter, each of the emulsifiable concentrates of the test compounds was diluted with water and sprayed on the cucumber at a rate of 7 ml per pot. One day and 7 days after the spraying, the leaves were inoculated with the mycelial disc (5 mm in diameter) of *Botrytis cinerea*. After 3 more days, the infectious state was observed. The degree of infection was examined by measuring the diameter of infected area, and the disease severity was calculated according to the following equation:

$$\text{Disease severity (\%)} = \frac{\text{Mean diameter of infected area in treated plot}}{\text{Mean diameter of infected area in untreated plot}} \times 100$$

The results of this test are shown in Table 3. As is apparent from the test results, the compounds of the present invention showed a higher protective activity than the control compounds and did not show phytotoxicity at all.

Table 3

| Test compound | Concentration of active ingredient (ppm) | Day elapsed from spraying to inoculation | Disease severity (%) | Phytotoxicity |
|---|---|---|---|---|
| 1 | 500 | 7 | 7.6 | — |
|   | 100 | 1 | 0 | — |
|   | 25 | 1 | 12.8 | — |
| 2 | 500 | 7 | 0 | — |
|   | 100 | 1 | 0 | — |
|   | 25 | 1 | 2.5 | — |
| 3 | 500 | 7 | 0 | — |
|   | 100 | 1 | 0 | — |
|   | 25 | 1 | 0 | — |
| 4 | 500 | 7 | 0 | — |
|   | 100 | 1 | 0 | — |
|   | 25 | 1 | 0 | — |
| 5 | 500 | 7 | 0 | — |
|   | 100 | 1 | 0 | — |
|   | 25 | 1 | 0 | — |
| 6 | 500 | 7 | 0 | — |
|   | 100 | 1 | 0 | — |
|   | 25 | 1 | 3.1 | — |

Table 3-continued

| Test compound | Concentration of active ingredient (ppm) | Day elapsed from spraying to inoculation | Disease severity (%) | Phytotoxicity |
| --- | --- | --- | --- | --- |
| [structure with Cl, Cl, N, C=O, CH₃, C=O] *1) | 500<br>100<br>25 | 7<br>1<br>1 | 82.3<br>0<br>10.6 | +++<br>—<br>— |
| [structure with Cl, Cl, N, C=O, C=O] *2) | 500<br>100<br>25 | 7<br>1<br>1 | 0<br>0<br>36.9 | ++<br>—<br>— |
| [benzimidazole structure with CONHC₄H₉ and CNHCOCH₃] *3) | 500<br>100<br>25 | 7<br>1<br>1 | 13.1<br>0<br>9.8 | —<br>—<br>— |
| No treatment | — | — | 100 | — |

Note:
*1) Compound disclosed in U.S. Pat. No. 3,741,981;
*2) Compound disclosed in U.S. Pat. No. 3,586,697;
*3) Commercially available fungicide, generic name "Benomyl".

EXAMPLE 5

Protective activity test on black spot of chinese cabbage (*Alternaria bracissicola*):

When chinese cabbage (var.: Nozaki No. 2) was grown up to a second true leaf stage in a flower pot of 9 cm in diameter, each of the wettable powders of the test compounds was diluted with water and sprayed on the chinese cabbage at a rate of 7 ml per pot. After 1 day, the leaf surface was inoculated by spraying a spore suspension of *Alternaria bracissicola*. After the inoculation, the chinese cabbage was placed in a dark and humid chamber for 1 day and then exposed to light for 2 days. The infectious state was then examined. The degree of infection was examined by the following method: the leaves examined were measured for a percentage of infected area and classified into the corresponding disease indices, 0, 1, 2, 3, 4; the leaves belonging to the same disease indices were summed up, $n_0$, $n_1$, $n_2$, $n_3$, $n_4$; and the disease severity was calculated according to the following equation.

| Disease index | Percentage of infected area |
| --- | --- |
| 0 | No infection |
| 1 | Infected area of less than 5% |
| 2 | Infected area of 5 to less than 30% |
| 3 | Infected area of 30 to less than 60% |
| 4 | Infected area of 60% or more |

$$\text{Disease severity (\%)} = \frac{0 \times n_0 + 1 \times n_1 + \ldots + 4 \times n_4}{4 \times n} \times 100$$

The results of this test are shown in Table 4.

Table 4

| Test compound | Concentration of active ingredient (ppm) | Disease severity (%) |
| --- | --- | --- |
| 1 | 500 | 8.3 |
| 2 | 500 | 5.2 |
| 3 | 500 | 2.1 |
| 4 | 500 | 1.7 |
| 5 | 500 | 1.5 |
| 6 | 500 | 4.3 |
| No treatment | — | 100 |

EXAMPLE 6

Protective activity test on Alternaria leaf spot of apple (*Alternaria mali*):

A 3-year old seedling of apple (var.: Indo) cultivated in a flower pot of 30 cm in diameter was used as a test plant. Each of the emulsifiable concentrates of the test compounds was diluted with water to a required concentration. When each seedling shot out three to four young branches having 10 to 20 young leaves thereon, the prepared aqueous solution was sprayed thereon at a rate of 30 ml per seedling. After the spraying, the seedling was cultivated in a greenhouse for 6 days. The whole body of the seedling was then inoculated by spraying a spore suspension of *Alternaria mali*. The seedling was then placed in a humid chamber for 24 hours and then in a greenhouse for 2 days. The infectious state was then examined. The degree of infection was examined by the following method: the leaves examined were measured for a percentage of infected area and classified into the corresponding disease indices, 0, 1, 2, 3, 4, 5; the leaves belonging to the same disease indices were summed up, $n_0$, $n_1$, $n_2$, $n_3$, $n_4$, $n_5$; and the disease severity was calculated according to the following equation.

| Disease index | Percentage of infected area |
| --- | --- |
| 0 | No infection |
| 1 | Infected area of less than 10% |
| 2 | Infected area of 10 to less than 20% |
| 3 | Infected area of 20 to less than 40% |
| 4 | Infected area of 40 to less than 60% |
| 5 | Infected area of 60% or more |

$$\text{Disease severity (\%)} = \frac{0 \times n_0 + 1 \times n_1 + \ldots + 5 \times n_5}{5 \times n} \times 100$$

The results of this test are shown in Table 5. As is apparent from the test results, the compounds of the present invention show a higher protective activity than the control compound.

Table 5

| Test compound | Concentration of active ingredient (ppm) | Disease severity (%) |
| --- | --- | --- |
| 1 | 500 | 14.3 |
| 2 | 500 | 9.4 |
| 3 | 500 | 2.3 |
| 4 | 500 | 0.6 |
| 5 | 500 | 1.7 |
| 6 | 500 | 1.0 |
| *) | 500 | 26.4 |
| No treatment | — | 63.7 |

Note:
*) Commercially available fungicide, generic name "Captafol".

EXAMPLE 7

Effect of controlling rice Helminthosporium leaf spot (*Cochliobolus miyabeanus*):

Rice plants (var.: Waseasahi), which had been cultivated to a 4 leaves stage in flower pots of 9 cm in diameter, were individually sprayed with 10 ml per pot of an aqueous dilute solution of each of the test compounds in the form of a wettable powder. After 7 days, the rice plants were sprayed and inoculated with a spore suspension of rice leaf spot fungus (*Cochliobolus miyabeanus*). Three days thereafter, the number of diseased spots generated was counted to investigate the fungicidal effect of each compound, whereby the results shown in Table 6 were obtained. As seen in Table 6, the compounds of the present invention showed markedly excellent effects as compared with the control compounds.

Table 6

| Test compound | Active ingredient concentration (ppm) | Number of spots per leaf |
| --- | --- | --- |
| 1 | 500 | 8.3 |
| 2 | 500 | 0 |
| 3 | 500 | 0 |
| 4 | 500 | 2.4 |
| 5 | 500 | 3.2 |
| 6 | 500 | 10 |

Table 6-continued

| Test compound | Active ingredient concentration (ppm) | Number of spots per leaf |
| --- | --- | --- |
| *1) | 500 | 19 |
| *2) | 500 | 14 |
| *3) | 500 | 20 |
| No treatment | — | 79 |

Note:
*1) Compound disclosed in U.S. Pat. No. 3,741,981;
*2) Compound disclosed in U.S. Pat. No. 3,586,697;
*3) Commercially available fungicide, generic name "Edifenphos".

EXAMPLE 8

Antimicrobial activity test on industrial molds:

The growth-inhibiting effect of the compounds of the present invention on *Aspergillus niger* ATCC 6275, *Cladosporium herbarum* IAM F517 and *Chaetomium globosum* ATCC 6205 which propagate in industrial products and the like and cause damage therein, was examined according to the agar dilution method. The results are shown in Table 7.

Table 7

| Test compound | Effective concentration (ppm) | | |
| --- | --- | --- | --- |
| | A. niger | C. herbarum | C. globosum |
| 1 | 2000 | 2000 | 2000 |
| 2 | 1000 | 1000 | 1000 |
| 3 | 1000 | 1000 | 1000 |
| 4 | 1000 | 1000 | 1000 |
| 5 | 1000 | 1000 | 1000 |
| 6 | 1000 | 1000 | 1000 |

What is claimed is:

1. A compound of the formula:

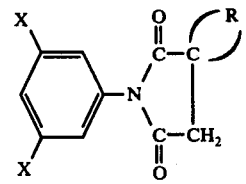

wherein X is a chlorine or bromine atom and R is a $C_3$–$C_6$ alkylene group.

2. The compound according to claim 1, wherein X is a chlorine atom and R is a tetramethylene group.

3. The compound according to claim 1, wherein X is a chlorine atom and R is a pentamethylene group.

4. A fungicidal composition which comprises as an active ingredient a fungicidally effective amount of a compound of the formula:

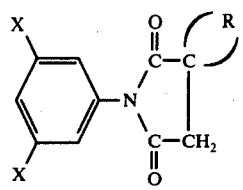

wherein X is a chlorine or bromine atom and R is a C₃–C₆ alkylene group and an inert carrier.

5. A method for controlling fungi which comprises applying to the fungi a fungicidally effective amount of a compound of the formula:

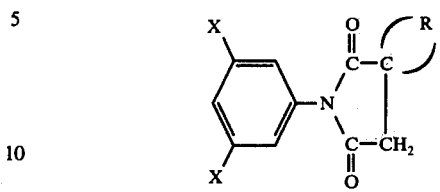

wherein X is a chlorine or bromine atom and R is a C₃–C₆ alkylene group.

* * * * *